US00PP27383P3

(12) United States Plant Patent
MacGregor et al.

(10) Patent No.: US PP27,383 P3
(45) Date of Patent: Nov. 15, 2016

(54) ***ANEMONE* PLANT NAMED 'MACANE007'**

(50) Latin Name: ***Anemone* hybrid**
Varietal Denomination: MACANE007

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 127 days.

(21) Appl. No.: 14/544,128

(22) Filed: Nov. 28, 2014

(65) Prior Publication Data

US 2016/0157404 P1 Jun. 2, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP23,132 P2 * 10/2012 MacGregor et al. ..... Plt./263.1

* cited by examiner

*Primary Examiner* — Anne Grunberg
(74) *Attorney, Agent, or Firm* — Cassandra Bright

(57) ABSTRACT

A distinct new cultivar of *Anemone* plant named 'MACANE007', characterized by a long flowering season, tall plant habit and semi-double flowers. The new cultivar is an *Anemone* typically suited for ornamental container and landscape use.

2 Drawing Sheets

Latin name of the genus and species: *Anemone* hybrid.
Variety denomination: 'MACANE007'.

BACKGROUND OF THE INVENTION

The new *Anemone* was discovered by the inventors, Elizabeth and Alasdair MacGregor, as part of a breeding program, using *Anemone* hybrids as parents. The seed parent is an unpatented, proprietary *Anemone* hybrid which was crossed with the unpatented *Anemone* hybrid 'Pamina'. The cross was made in 2005, and the selection of the new variety made during 2008, at a commercial nursery, in Kirkcudbright, Scotland.

Asexual reproduction by tissue culture has been undertaken in 2008, by at a commercial laboratory in the Netherlands. Plants produced have proved to be stable and reproduced true to type in successive generations.

SUMMARY OF THE INVENTION

The cultivar 'MACANE007' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MACANE007'. These characteristics in combination distinguish 'MACANE007' as a new and distinct *Anemone* cultivar:

1. Continuous flowering season from Mid June until Fall.
2. Semi-double, white flowers, with blue under side coloration to flower.
3. Tall plants, with a height of 70 to 80 cm.

PARENTAL COMPARISON

Plants of the new cultivar 'MACANE007' are similar to the seed parent in most horticultural characteristics. However, plants of 'MACANE007' differ in that they produce semi-double two toned flowers, whereas the seed parent produces single, pure white flowers.

Plants of the new cultivar 'MACANE007' are similar to the pollen parent in most horticultural characteristics. However, plants of 'MACANE007' differ in that they produce semi-double two toned flowers, whereas the pollen parent produces fully double deep pink flowers.

COMMERCIAL COMPARISON

Plants of the new cultivar 'MACANE007' are similar to the known commercial variety, *Anemone hybrida* 'Honorine Jobert', unpatented, in some horticultural characteristics. However, plants of 'MACANE007' differ in the following:

1. 'MACANE007' begins flowering in June, 'Honorine Jobert' begins flowering in August.
2. 'MACANE007' begins produces two toned flowers, whereas 'Honorine Jobert' produces pure white flowers.
3. Plant habit of the new variety is clump forming, whereas 'Honorine Jobert' plants are trailing/spreading.

Plants of the new cultivar 'MACANE007' are similar to the known commercial variety, *Anemone multifida* 'Macane001' U.S. Plant Pat. No. 23,132 in some horticultural characteristics. However, plants of 'MACANE007' differ in that they are on average 15 cm taller and begin flowering two to three weeks later. Additionally, the new variety produces different foliage and a different flower coloration pattern than 'Macane001'.

BRIEF DESCRIPTION OF THE PHOTOGRAPHS

Figure 1:
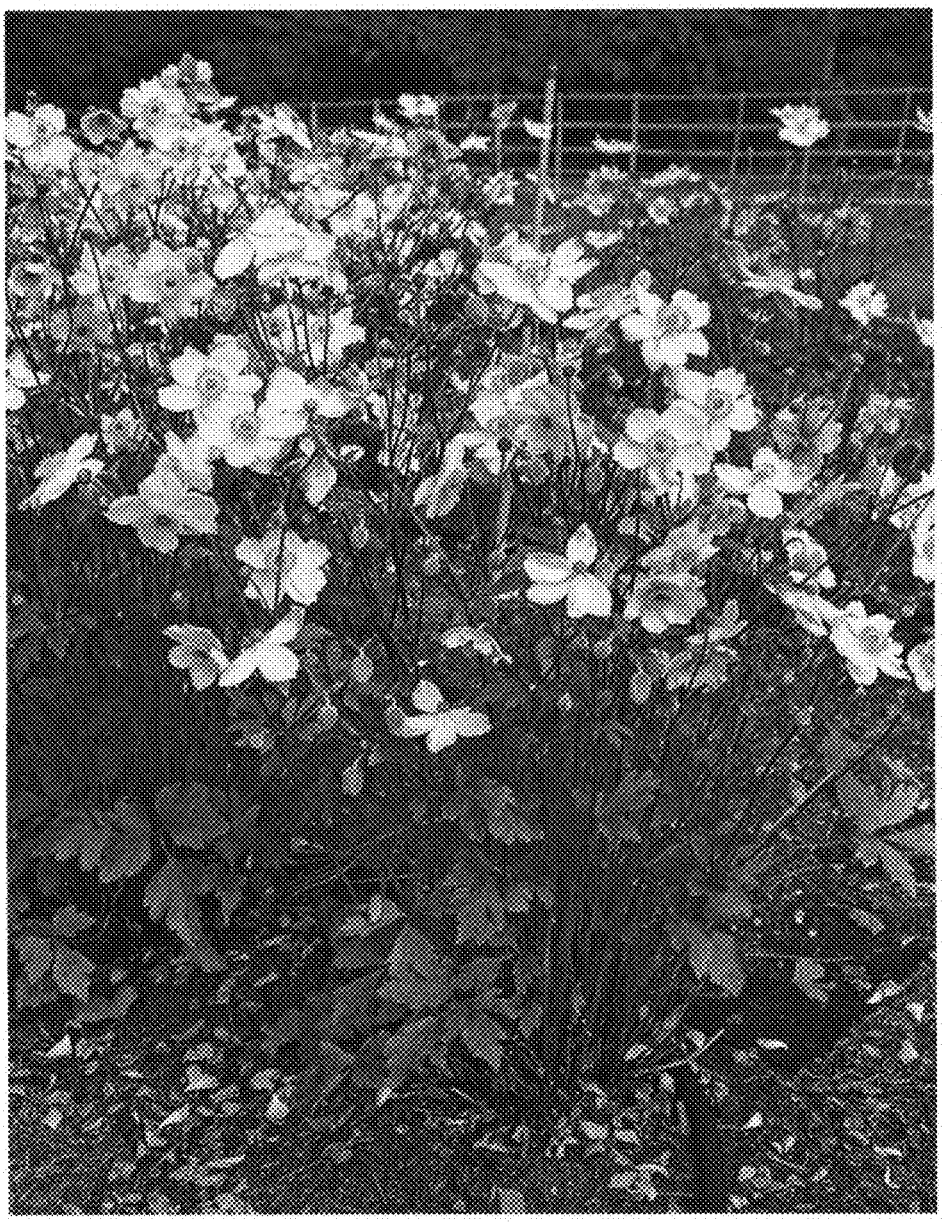

The accompanying photograph in FIG. 1 illustrates in full color a typical plants of 'MACANE007' grown outdoors in a garden in Kirkcudbright, Scotland. This plant is approximately 15 months old.

Figure 2:
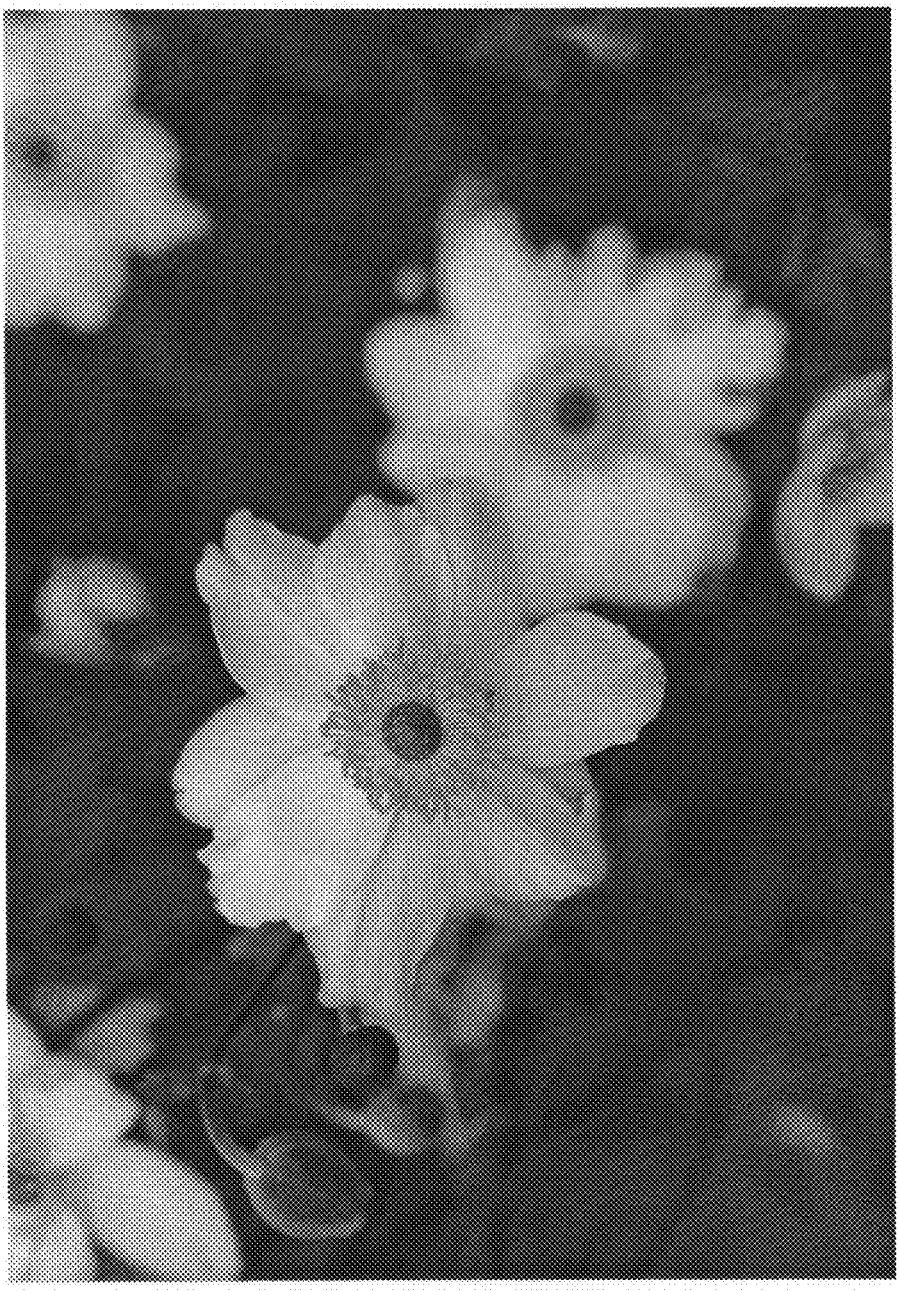

FIG. 2 illustrates a close up of the flower and flower bud.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'MACANE007' plants grown outdoors in Kirkcudbright, Scotland at a commercial nursery. The growing temperature ranged from 0° C. to 12° C. at night to 8° C. to 22° C. during the day. During the winter period December to March, plants were sheltered in a large poly-tunnel with day temperatures ranging from 5° C. to 18° C., and night temperatures ranging from −5° C. to 8° C. No artificial light, photoperiodic treatments or chemical treatments were given to the plants. Measurements and numerical values represent averages of typical flowering types.

Botanical classification: *Anemone* hybrid 'MACANE007'.

Age of the plant described: Approximately 15 months.

Container size of the plant described: 2 liter commercial container.

PROPAGATION

Time to produce a flowering plant from root-cutting: Nine to twelve months.

Root description: Fibrous, reddish-brown (not R.H.S. identified) in color.

Rooting habit: Dense, freely branching.

PLANT

Growth habit: Upright.

Pot size of plant described: 2 liter circular pot (14 cm).

Height: 34 cm.

Plant spread: 33.5 cm.

Growth rate: Moderate.

Branching characteristics: No lateral branches, flowering stems grow from a basal rosette.

Length of primary lateral branches: No lateral branches present, basal branching.

FOLIAGE

Leaf:

*Arrangement*.—Basal rosette.

*Leaflets*.—Shape: Trifoliate, broad ovate in outline. Quantity: Approximately 6 per basal rosette. Average Length: 10.3 cm. Average Width: 9.9 cm.

*Individual leaf blades*.—Shape of blade: Ovate. Apex: Short apiculate. Base: Acute to short attenuate. Margin: Biserrate.

*Texture of top surface*.—Very slightly glossy.

*Pubescence*.—Upper side sparsely covered with short adpressed hairs, average length: 0.05 cm, coloured near RHS White N155D, main veins and secondary veins on under side moderately covered with short adpressed hairs, average length: 0.05 cm, coloured near RHS Green-White 157D.

*Aspect*.—Leaf blades in an average angle of 75° to petiole.

*Color*.—Young foliage upper side: Near RHS Green 143A. Young foliage under side: In between near RHS Green143A and Yellow-Green 146B. Mature foliage upper side: Near RHS Green 137B. Mature foliage under side: Between RHS Yellow-Green 147C and Yellow-Green 148C.

*Venation*.—Type: Pinnate. Venation color upper side: Near RHS Yellow-Green 144C. Venation color under side: Near RHS Yellow-Green 144A.

*Petiole*.—Length: 18.5 cm. Diameter 0.2 cm. Color: Near RHS Yellow-Green 146B, moderately to heavily tinged 148A and Greyed-Purple 187C. Texture: Densely covered with short hairs, average length: 0.1 cm, colored near RHS White 155D.

*Stipule description* (*if present*).—Length: 1.8 cm. Diameter: 0.5 cm. Color: Near RHS 145C to 145D. Texture: Densely covered with short hairs, average length: 0.1 cm, colored near RHS N155D.

FLOWER

Natural flowering season: Midsummer until Fall.

Days to flowering from rooted cutting: 9-12 months.

Inflorescence and flower type and habit: Inflorescence a terminal corymb, individual flowers rotate, single.

Rate of flower opening: 14 to 21 days from bud to fully opened flower.

Flower longevity on plant: Approximately one week.

Persistent or self-cleaning: Self-cleaning.

Bud:

*Shape*.—Broad ovate.

*Length*.—1.1 cm.

*Diameter*.—1.0 cm.

*Color*.—Near RHS Yellow-Green 147D.

Flower size:

*Diameter*.—5.8 cm.

*Depth*.—1.5 cm.

*Aspect*.—Outward to slightly nodding.

Tepals: No separate petals and sepals present, these floral structures are referred to as "Tepals" here.

*Quantity*.—7.

*Arrangement*.—Rotate.

*Length*.—3.0 cm.

*Width*.—2.3 cm.

*Shape*.—Broad elliptic to slightly obovate.

*Apex*.—Obtuse to broad acute.

*Base*.—Broad cuneate.

*Margin*.—Entire.

*Texture, upper and lower surfaces*.—Glabrous, matte, slightly velvety.

*Color*.—When opening, upper surface: Near RHS N155C to N155D. When opening, lower surface: Near RHS Yellow-Green 145C, moderately tinged Violet 85C. Fully opened, upper surface: Near RHS N155C to N155D. Fully opened, lower surface: Near RHS N155C, slightly tinged Yellow-Green 145C and Violet 85C.

Bracts (if present): No bracts present.

Longest peduncles:

*Length*.—28.9 cm.

*Diameter*.—0.35 cm.

*Angle*.—About 90° to basal rosette.

*Strength*.—Moderately strong.

*Texture*.—Slightly glossy, densely covered with short soft hairs, average length: 0.1 cm, coloured near RHS N155D.

*Color*.—Near RHS Yellow-Green 146C, tinged Greyed-Purple 187A, 187B and 187C towards the base.

Shortest peduncles:

*Length*.—5.4 cm.

*Diameter*.—0.2 cm.

*Angle*.—About 35° to the peduncle.

*Strength*.—Moderately strong.

*Texture*.—Slightly glossy, densely covered with short soft hairs, average length: 0.075 cm, coloured near RHS N155D.

*Color*.—Near RHS 146C.

Fragrance: No fragrance.

REPRODUCTIVE ORGANS

Stamens:

*Number*.—Average: 250.

Anthers:

*Shape*.—Narrow kidney-shaped to oblong.

*Length*.—Approximately 0.2 cm.

*Color*.—Near RHS Yellow-Orange 14A.

*Pollen*.—Color: Near RHS Yellow-Orange 14A. Quantity: Very low.

Pistil:

*Number*.—Average: 250.

*Length*.—0.25 cm.

*Style*.—Length: 0.2 cm. Color: Near RHS Yellow-Green 144B.

*Stigma*.—Shape: Pointed. Color: Near RHS Yellow-Green 144C. Ovary Color: Near RHS Yellow-Green 144C.

OTHER CHARACTERISTICS

Seed/fruit: No seeds/fruits detected to date.

Temperature tolerance: Plants of the new *Anemone* h are hardy to at least USDA Zone 6.

Diseases and pests: Neither resistance nor susceptibility to normal diseases and pests of *Anemone* has been observed.

What is claimed is:

1. A new and distinct cultivar of *Anemone* hybrid plant named 'MACANE007' as herein illustrated and described.

* * * * *